(12) United States Patent
Aryal et al.

(10) Patent No.: US 9,371,166 B2
(45) Date of Patent: Jun. 21, 2016

(54) OXYGEN GENERATING BOTTLE

(71) Applicant: AVENT, INC., Alpharetta, GA (US)

(72) Inventors: Shruti Aryal, Beaverton, OR (US); Richard Daniel Pike, Alpharetta, GA (US); Jon N. Neese, Oregon City, OR (US)

(73) Assignee: Avent, Inc., Alpharetta, GA (US)

( * ) Notice: Subject to any disclaimer, the term of this patent is extended or adjusted under 35 U.S.C. 154(b) by 155 days.

(21) Appl. No.: 13/729,197

(22) Filed: Dec. 28, 2012

(65) Prior Publication Data

US 2014/0186463 A1    Jul. 3, 2014

(51) Int. Cl.
| | |
|---|---|
| *B67D 7/76* | (2010.01) |
| *A62B 7/08* | (2006.01) |
| *B65D 51/24* | (2006.01) |
| *A45D 34/00* | (2006.01) |
| *A61K 8/66* | (2006.01) |
| *A61K 8/04* | (2006.01) |
| *A61K 8/19* | (2006.01) |
| *A61K 8/22* | (2006.01) |
| *A45D 34/04* | (2006.01) |

(52) U.S. Cl.
CPC ............... *B65D 51/24* (2013.01); *A45D 34/00* (2013.01); *A61K 8/046* (2013.01); *A61K 8/19* (2013.01); *A61K 8/22* (2013.01); *A61K 8/66* (2013.01); *A45D 34/04* (2013.01); *A45D 2200/056* (2013.01); *A61K 2800/87* (2013.01); *A61K 2800/882* (2013.01)

(58) Field of Classification Search
CPC ....................................................... B65D 51/24
USPC ........................................... 422/122; 222/190
See application file for complete search history.

(56) References Cited

U.S. PATENT DOCUMENTS

| | | | |
|---|---|---|---|
| 4,921,170 A * | 5/1990 | Grollier | 239/304 |
| 5,736,582 A | 4/1998 | Devillez | |
| 6,375,902 B1 * | 4/2002 | Moini et al. | 423/219 |
| 8,450,294 B2 * | 5/2013 | Lepilleur et al. | 514/54 |
| 2006/0121101 A1 | 6/2006 | Ladizinsky | |
| 2013/0014534 A1 * | 1/2013 | Jang | C01B 13/0214 62/331 |
| 2013/0175296 A1 * | 7/2013 | Gray et al. | 222/135 |

FOREIGN PATENT DOCUMENTS

| | | | |
|---|---|---|---|
| GB | 2024049 A * | 1/1980 | |
| WO | WO 2011/075657 A2 | 6/2011 | |

* cited by examiner

*Primary Examiner* — Kevin Joyner
(74) *Attorney, Agent, or Firm* — Dority & Manning, P.A.

(57) ABSTRACT

There is provided a system for delivering an oxygen rich lotion. The system uses a single reservoir dispensing bottle that contains a peroxide-rich liquid. The bottle has an outlet within which is a peroxide decomposition catalyst immobilized on a substrate, so that the peroxide-rich liquid and immobilized catalyst come in contact with each other just as the liquid is leaving the outlet of the bottle.

10 Claims, 1 Drawing Sheet

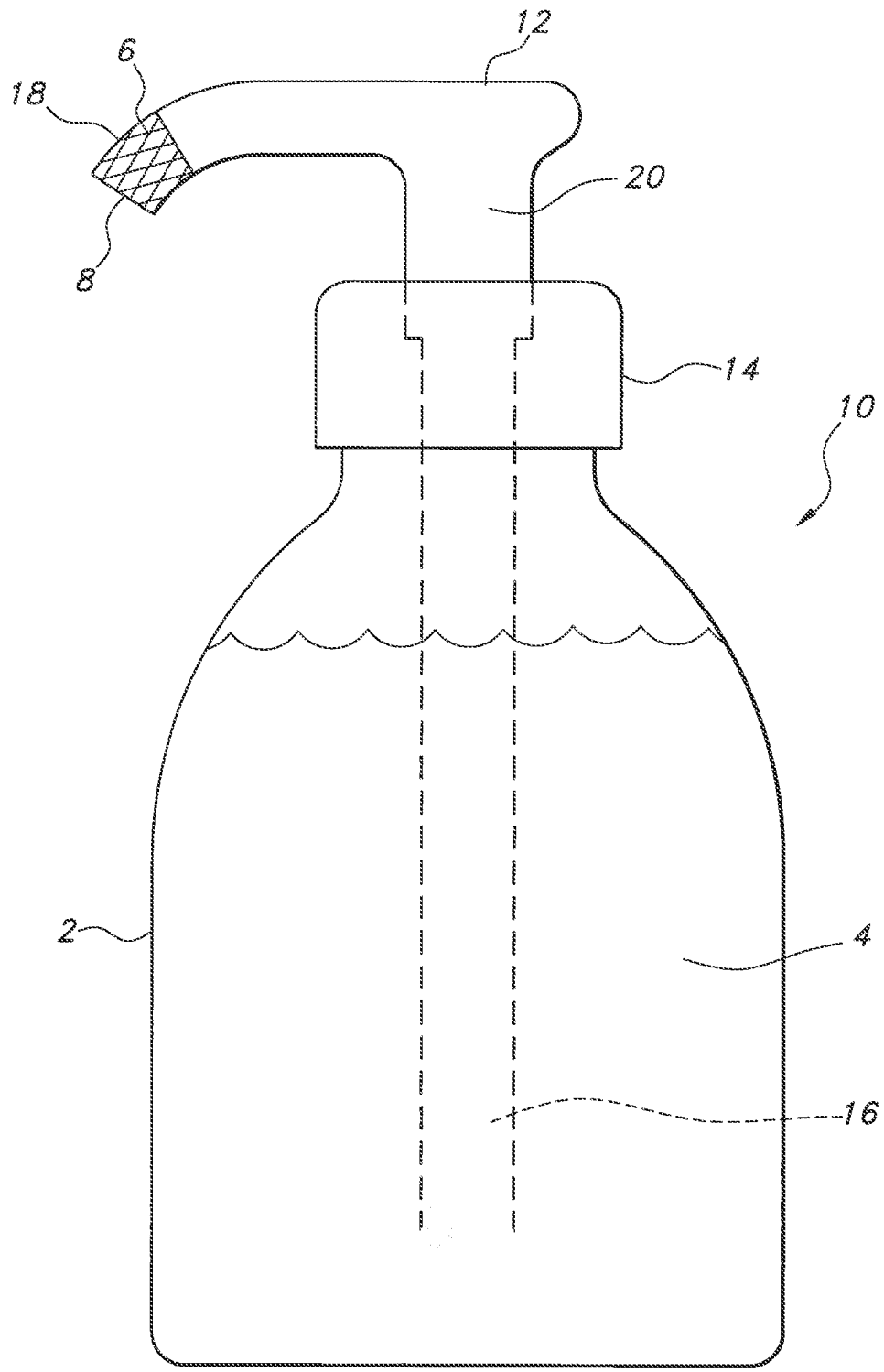

OXYGEN GENERATING BOTTLE

The present disclosure relates to the provision of oxygen for use in cosmetic formulations.

The lack of oxygen, i.e. hypoxia, is commonly experienced by people in their extremities as they get older due to poor blood circulation as well as by those with conditions such as diabetes. Studies have also shown below normal, low oxygen tension in the skins of older people. This often leads to poor skin health and an excessive presence of visible conditions such as wrinkles, dryness and lower skin elasticity. Over the years, cosmetic manufacturers have introduced skin formulations with a large variety of ingredients such as emollients, exfoliators, moisturizers etc., to retard these age related effects and improve and maintain skin health. Attacking the problem of low oxygen directly has not been generally practiced.

The delivery of oxygen to the skin for common use is a technological challenge, since oxygen tends to be reactive. High concentrations of oxygen are a concern for home use since this reactive natural can lead to rapid combustion. Low but effective concentrations of oxygen for therapeutic use can, however, be provided in the form of a peroxide and a peroxide decomposition catalyst per U.S. patent publication 2006/0121101 to Ladizinsky. This publication provides such a treatment for intact skin through the use of a dressing that is applied to an area of the skin. The dressing generally has a rupturable reservoir containing an aqueous hydrogen peroxide composition and a hydrogel layer having a peroxide decomposition catalyst. Unfortunately the catalytic decomposition of hydrogen peroxide to oxygen is quite rapid and so the dressing has a layer that is impermeable to oxygen on the outside so that the oxygen is held against the skin for the maximum time possible. While this dressing is useful for small areas of the skin, it should be clear that it is unworkable for large areas or irregularly shaped areas of skin.

Alternatively, Devillez (U.S. Pat. No. 5,736,582) proposes the use of hydrogen peroxide in the place of benzoyl peroxide in skin treatment compositions that also contain solvents for hydrogen peroxide. This allows the hydrogen peroxide to stay below a level that will damage the skin and to stay in solution in greater concentrations. A solvent such as dimethyl isosorbide along with water is taught as being effective. No peroxide decomposition catalyst is present. Unfortunately, no data on oxygen concentration or generation are given, nor is the time required for oxygen liberation. While this method appears to be an advance over non-oxygen containing compositions, the lack of data makes it difficult to make objective judgments on the overall effectiveness of this approach. Given the concentrations of peroxide, however, it is doubtful that significant volumes of oxygen were generated.

Applying oxygen to the skin topically through the application of a liquid or foam composition is a convenient, easy and quick method of delivering the desired benefits discussed above. A peroxide and a peroxide decomposition catalyst, packaged separately and combined at the time of use could deliver these benefits. A two part formulation helps to ensure that the oxygen is available for use and has not been lost during storage, but this approach presents challenges for product developers because of the need to keep the two ingredients separate and combine them at the time of use, like a two part epoxy. Two component bottles having one liquid reservoir for the peroxide component and another liquid reservoir for the catalyst component have been developed, but are expensive since they require special manufacturing techniques and valving to combine the formulation ingredients properly.

There is a need for an easy-to-use way to apply oxygen to the skin. Such a method and/or product should be inexpensive, have relatively few components and be intuitive to use, without the need for special bottle designs, dressings or other awkward requirements. A product that may be used in a manner similar to known products would be most readily accepted by the consumer.

SUMMARY

The problem discussed above has found a solution to a large degree in the present disclosure, which describes the use of a lotion dispensing bottle system that can generate oxygen as part of the dispensing. The oxygen is released or "liberated" from combining ingredients within the bottle system; the ingredients are kept separated until predetermined amounts of the ingredients are combined via a dispensing action that results in a dispensed lotion in the form of a liquid or foam that is oxygenated.

There is disclosed a system for delivering an oxygen-rich lotion. The system has a reservoir of a peroxide-rich liquid and this reservoir makes up most of the bottle system. The bottle system has an outlet within which is a peroxide decomposition catalyst (the catalyst) immobilized on a substrate, so that the peroxide-rich liquid and immobilized catalyst come in contact before the liquid leaves the outlet and exits the bottle system.

The catalyst may desirably be catalase, manganese dioxide ($MnO_2$) or a base such as sodium carbonate ($Na_2CO_3$) and the peroxide is desirably hydrogen peroxide. The peroxide is desirably present at a concentration of about 1 weight percent in a water-in-oil emulsion.

The catalyst is contained on or supported by a substrate that has an open structure to allow the peroxide-rich liquid to flow through it and ensure good contact with the catalyst. The substrate may be a mesh, foam, woven or nonwoven material, or other suitable porous material. The substrate is desirably an open celled foam made from plastics, cellulose and the like; more desirably open celled polyurethane foam.

The catalyst may also be on a constrained mobile substrate having a structure like beads, spheres, extrudates, powders, grains and pellets that are constrained so that the substrate may not leave the dispensing bottle.

To impart additional cosmetically desirable properties, the component compositions may contain other ingredients such as natural or synthetic polymers, moisturizers, humectants, viscosity modifiers, emollients, texture enhancers, UV blocking agents, colorants, pigments, ceramics (fumed silica, titanium dioxide, natural and synthetic clays), antioxidants, fragrances etc.

BRIEF DESCRIPTION OF THE DRAWINGS

FIG. 1 is an exemplary pump-type system for delivering an oxygen-rich lotion shown in cross-sectional view.

DETAILED DESCRIPTION

Reference will now be made in detail to one or more embodiments of the invention, examples of the invention, examples of which are illustrated in the drawings. Each example and embodiment is provided by way of explanation of the invention, and is not meant as a limitation of the invention. For example, features illustrated or described as part of one embodiment may be used with another embodiment to yield still a further embodiment. It is intended that the invention include these and other modifications and variations as coming within the scope and spirit of the invention.

The disclosed oxygen generating system uses a dispensing bottle that has a reservoir for the peroxide-rich (lotion) component. The catalyst is immobilized on a substrate and placed near or in the liquid outlet, e.g. nozzle, of the bottle. Such placement has the peroxide and catalyst come in contact with each other as the liquid leaves the outlet of the bottle or immediately before these mixed components leave the system. In all embodiments the mixed components (peroxide in contact with catalyst) are kept segregated from the reservoir of peroxide-rich lotion. Oxygen is generated after the peroxide-rich liquid and catalyst contact each other. The bottle may be any of those commonly used to dispense liquid; squeeze bottles, pump bottles and aerosol bottles.

It is also possible, though less desirable, to immobilize a peroxide material, including peroxide derivatives, in the outlet of the system and mix the catalyst with a lotion and retain the latter in the reservoir of the bottle system, though this has not been optimized.

FIG. 1 shows an exemplary pump dispensing bottle 2. The bottle includes a pump 20 and the pump has an inlet or suction 16 is in fluid communication with the liquid reservoir 4 and is open at a distal end. The bottle 2 has a cap 14 that may desirably screw onto the bottle 2. The user pushes an exposed portion 12 of the pump 20 to transfer peroxide-rich liquid from the reservoir 4, forcing the liquid into and through the catalyst 6 and any related containing substrate 18, and out of the outlet 8 on the proximal end to the user.

The catalyst may be any of those known to decompose peroxide that are safe of use on the skin, since it is possible that a small amount of catalyst may detach or be eroded from its substrate. The catalyst in any of the embodiments may be catalase, manganese dioxide ($MnO_2$) or a base such as sodium carbonate ($Na_2CO_3$). The catalyst catalyzes the reaction from hydrogen peroxide to oxygen and water. Manganese dioxide may be used if the user is less concerned about the treated area being seen since this type of catalyst may result in a dispensed lotion that leaves a visible residue. For example, if the human skin to which the oxygen is to be applied is in a less visible area or if it is desired to apply the oxygen to a non-human animal, a dark residue may not be preferred. The catalyst is immobilized on a substrate such that most of the catalyst is retained within the system.

The catalyst carrier, support or substrate 18 should be an open structure to allow the peroxide containing liquid to flow through the structure and ensure good contact with the catalyst. Any open structure on which the catalyst may be immobilized may be used as a substrate. These include meshes (e.g. wire meshes), foams, woven structures, and nonwoven materials like spunbond fabrics. Materials for such structures include metals, glass (including glass fibers), ceramics and plastics. Open celled foams may be made from plastics, cellulose and the like. Foams made from polyurethane are desirable.

Alternatively the substrate may also be small, mobile structures that are constrained so that the substrate may not leave the dispenser, e.g., beads within a cage having openings smaller than the beads. Examples of other suitable mobile substrates that may be constrained include spheres, extrudates, powders, grains and pellets. These mobile structures may be made from metals, glass, ceramic and plastics.

The following are methods of coating a substrate with a catalyst:

EXAMPLE 1

Method of Coating Foam with Manganese Oxide Particles 4 g of manganese (IV) oxide (Sigma, reagent grade, 10 micron) was first mixed with 195 g of de-ionized (DI) water in a plastic beaker. The solution was mixed with a high speed mixer. 4 g of Dur-O-Set Elite Ultra Soft (Celanese emulsion polymer) was then added to the solution and stirred for 1 min. The mixer was removed and set aside for 5 min. The solution was poured into a flat plastic container that held the fluid at no more than 2 to 3 inches in depth. There should be enough fluid to completely submerge the substrate material. The container should be of appropriate shape to withstand the shaking of the shaker. If using conical tubes as containers, one might want to use an appropriately sized tube rack and attach it firmly to the shaker so that the tubes don't fall off or become detached.

Once an appropriately sized container is chosen for the manganese oxide coating solution, small pieces of open celled polyurethane foam (1 lb-1.2 lb./cubic feet) and/or cellulose foam (Scotch brite dish washing foams) are cut with a cutting die to form substrate material. The foam pieces (8-10 at a time) were then submerged in the manganese IV oxide fluid and allowed to soak for 1-2 hours while shaking. After 2 hours of shaking, the pieces are gently removed with tweezers and excess fluid is drained into another container, the pieces are then placed onto a polypropylene mesh to be placed in oven and dried at 55 degree C. until completely dried. Alternatively, the coated pieces may be air dried in room temperature until they are completely dry.

EXAMPLE 2

Method of Coating Foam with Catalase

A catalase solution (from Bio-Cat Inc.) is diluted in a buffer solution to approximately 2000 U. Note that Units of activity (U) are typically used to describe enzyme catalytic activity, where a unit (U) refers to the amount of enzyme that catalyzes the conversion of 1 micromole (µmole) of substrate per minute. Thus, 1 enzyme unit (U)=1 µmol/min, where µmol refers to the amount of substrate converted. Because each enzyme has a unique substrate, a unit of activity is different for one enzyme versus another. In addition, the experimental conditions under which enzymatic activity is determined must be specified (e.g., substrate concentration, temperature, pH, ionic strength, etc.). The SI unit of enzyme catalytic activity is the katal but it is less commonly used in practice. 1 katal=amount of enzyme that catalyzes the conversion of 1 mole of substrate per second (1 katal=1 mol/s). Thus, 1 Unit=$1.667 \times 10^{-8}$ katal and 1 katal=$6.00 \times 10^7$ Units.

The foam pieces (cut out similar to Example 1) are dipped in the diluted solution. Without drying, the catalase coated foam substrate material was inserted inside the cartridge (e.g. a PP tube, as is described subsequently).

EXAMPLE 3

Method of Coating Foam with Manganese Dioxide Nano Suspension

Split a 7.5×4 ⅛ in (19 by 1.6 cm) cellulose antimicrobial sponge in half horizontally. Cut twelve circular pieces from one half of the sponge using a no. 10 cutting die. Put the circular pieces of sponge in a plastic container. Add 200 ml of 0.1 M potassium permanganate solution to the container.

Place the plastic container containing the solution and the cellulose pieces onto an orbital shaker at 100 rpm. Let shake for 15 min. Measure 9 g of ethanol into a beaker. Using a transfer pipette slowly drop the ethanol into the solution that is shaking. Add the ethanol over a five minute time period and drop in random places around inside the container. Let shake for 2 hours. Observe the color change from purple to dark brown. Remove each piece from the container one by one using a tweezers at a sink. Remove the excess liquid, if any, by shaking or tapping. Then place the pieces onto a paper towel or tissue. Cover with another layer of tissue. Then cover and store overnight. Dry in an oven at 52 degree C. for 1 hour or until completely dry. Remove and store in an air tight container.

These pieces of foam catalyst substrate were inserted in a cartridge a manner as described subsequently. In an optimized system, the manganese dioxide nano particles or the micron sized particles would be completely immobilized into the matrix of the foam.

After the catalyst is immobilized on the substrate the substrate must be placed in the outlet of the bottle system. Below is an example of placing the substrate in the liquid outlet via a cartridge component.

Cartridge Unit Example:

A small cartridge component was prepared by cutting a 15 mm diameter polypropylene tube segment (~2 inches) so that the segment fits with an outlet of a squeezable bottle (the length and diameter of the tube was chosen to tightly fit to a lotion bottle). The treated foam material was then inserted into the lumen of the PP tube segment. The cartridge unit comprises the treated foam and the PP tube. The cartridge unit fits onto the squeezable bottle at or before the outlet so that any lotion with peroxide (from the reservoir as the system as described below) must flow through the cartridge before exiting the system. As the lotion is squeezed out of the system, the peroxide would react with the catalyst in the cartridge, generating oxygen.

Reservoir Unit Example:

An empty squeezable lotion bottle with flexible side wall(s) comprises an enclosed space. The bottle has one opening at the top of the bottle, a neck adjacent the opening, and most of the enclosed space below the neck. When the bottle is in an upright position, the enclosed space below the neck contains the reservoir and the reservoir, due to gravity, is kept separate from the neck. The reservoir is a volume of peroxide-rich lotion (liquid form).

Assembly of Cartridge and Reservoir

The cartridge example was inserted securely into the neck of the lotion bottle that contains the reservoir example. A suitable cap, e.g. screw-on type that mates with the lotion bottle outlet, was then placed on top of the lotion bottle to cover most of the opening. The cap had a small hole to let out the lotion as the lotion is squeezed through the catalyst containing cartridge and out of the bottle. As the lotion passed through the treated foam substrate material, hydrogen peroxide in the lotion reacted upon contact with the catalyst to generate oxygen. Oxygen-rich lotion was then delivered from the bottle outlet to the hand/skin of the person.

Exemplary Foams:

The foams for the Examples were chosen because of their resilient structure and porosity to allow fluid to pass through with minimal resistance. Polyurethane foam was more desirable than cellulose because of its high porosity and non-adherence to the lotion. The lotion needs to be able to flow freely through the treated foam material so that lotion doesn't take too much time to squeeze out. The open structure of the foam should allow good contact between the lotion and the treated foam so that adequate oxygen is generated.

This could also be achieved via a carefully designed automated pump system. In an automated system a squeeze and pump process could be used to pass the lotion through the treated foam such that the excess lotion can be squeezed out and won't block the path for next round of use.

Peroxide-rich Lotion:

Hydrogen peroxide in an emulsion was made from an original concentration of 35% w/w hydrogen peroxide solution (Spectrum HY115; New Brunswick, N.J.) added to a commercially available lotion base (Evonik Industries, product 1564-06) to produce a final concentration of 0.9% w/w hydrogen peroxide.

Alternatively, a water-in-oil emulsion may be made to which the hydrogen peroxide solution may be added to reach a final concentration of 0.9%-1% hydrogen peroxide in the emulsion. To prepare a water-in-oil emulsion, a first aqueous mixture consisting of water with water soluble thickeners and surfactants is made. An oil phase consisting of different types of oils and oil soluble surfactants/emulsifiers is also prepared. The water with thickeners and surfactants is slowly added to the oil phase containing the emulsifiers with stirring. 35% hydrogen peroxide may be pre-diluted or added straight to the emulsion depending on the volume of liquid desired to reach a desired viscosity of the emulsion, desirably >100,000 cps.

In an alternative embodiment, an aqueous phase mixture was prepared with 4% hydroxy ethyl cellulose (HEC) by mixing 12 g HEC to 300 g of de-ionized water. After mixing the slurry, the mixture was heated to 80 degree C. to activate the HEC so that it thickened. Then the suspension was cooled to room temperature. Alternatively, other thickeners such as carboxymethyl cellulose or Carbomers, guar gum, xanthan gum or combination of one or the others may also be used. Some thickeners may make slightly acidic suspensions and may need to be neutralized by addition of a base. The final pH of the thickener should be checked and be made neutral or close to neutral (5.5-7).

The oil phase was prepared using silicone oil with jojoba oil and lecithin (emulsifier) up to 1.5% purchased from "making cosmetics" website. In one particular instance, Aerosil 816R silica (hydrophobic nano-silica particle from Evonik) was also added for up to 2% by weight in the final oil mixture. This nano-silica was added to enhance the stabilization of the emulsion and preserve the oxygen content of this phase, which will be the very inner core of the tablet. Other cosmetic oils, Perfluorodecalin oil or fragrances may also be used as long as the densities of the fluids are consistent and are miscible with one another.

For the preparation of water-in-oil emulsions, the oil phase components were added first in the following order with homogenization after adding the emulsifiers. First, oils were mixed, then lecithin is added and homogenized, then aerosol silica is added and the mixture homogenized. Finally, the water phase (prepared earlier ~4% HEC or other thickeners) is slowly added as the emulsion is mixed in high shear with a homogenizer (~10,000 rpm). The final concentration of the emulsion was 50%-55% oils and emulsifiers with the remainder of aqueous phase mix. The resulting emulsion was a thick viscoelastic fluid which rubbed into the skin upon application. To this, the 35% hydrogen peroxide solution was added to have 1% hydrogen peroxide in the final emulsion stock.

Alternative Example

An illustrative example for separation of the peroxide reservoir from the catalyst material in another pump bottle system embodiment includes:

a bottle base pump component with an inlet and an outlet that attaches to the bottle base and with an actuating plunger (piston)

one-way valve that physically seals the inlet of the pump that allows liquid into the pump component but not through the pump component conduit in fluid communication with the interior of the bottle base and the inlet of the valve peroxide reservoir held in the bottle base catalyst material is contained within the pump component.

This alternative example pump bottle system dispenses lotion from the pump component outlet similar to known pump bottles via these actions: an aliquot from the peroxide reservoir is transferred through the conduit and through the valve and into the pump component by retraction of a plunger (piston); the aliquot reacts upon contact with the catalyst material to generate oxygen in the pump component; the plunger (piston) is then actuated to dispense the oxygenated aliquot from the pump component. Actuation of the plunger can be delayed by a timing device or mechanically to ensure acceptable oxygen generation.

While the disclosure has been described in detail with respect to specific embodiments thereof, it will be apparent to those skilled in the art that various alterations, modifications and other changes may be made to the disclosure without departing from the spirit and scope of the present disclosure. It is therefore intended that the claims cover all such modifications, alterations and other changes encompassed by the appended claims.

What is claimed is:

1. A system for delivering an oxygen rich lotion, comprising a dispensing bottle, a reservoir that contains a peroxide-rich lotion comprising a base lotion mixed with a peroxide solution, the bottle having an outlet, a peroxide decomposition catalyst immobilized on a substrate and near the outlet, so that the peroxide-rich lotion and immobilized catalyst come in contact with each other via dispensing and before the liquid leaves the outlet of the bottle, the catalyst immobilized as a coated dried formulation on the substrate such that reaction between the catalyst and peroxide-rich lotion occurs as the peroxide-rich lotion flows through the substrate and contacts the immobilized catalyst; wherein the catalyst is immobilized such that unreacted catalyst remains immobilized on the substrate.

2. The system of claim 1 wherein said catalyst is catalase, manganese dioxide ($MnO_2$) or a base.

3. The system of claim 1 wherein said peroxide is hydrogen peroxide.

4. The system of claim 3 wherein said peroxide solution has peroxide present at a concentration of about 1 weight percent in a water in oil emulsion.

5. The system of claim 1 wherein said catalyst substrate is an open structure to allow the peroxide-rich lotion to flow through and ensure good contact with the catalyst.

6. The system of claim 5 wherein substrate is selected from the group consisting of mesh, foam, woven and nonwoven materials.

7. The system of claim 6 wherein the substrate is open celled foam made from one of plastics or cellulose.

8. The system of claim 7 wherein said substrate is open celled polyurethane form.

9. The system of claim 1 wherein said lotion further comprises any one or combination of natural or synthetic polymers, moisturizers, humectants, viscosity modifiers, emollients, texture enhancers, UV blocking agents, colorants, pigments, ceramics, antioxidants, and fragrances.

10. The system of claim 1 with a valve component that separates the reservoir from the catalyst.

* * * * *